United States Patent [19]

Hrubetz

[11] Patent Number: 4,971,074
[45] Date of Patent: Nov. 20, 1990

[54] DEVICE FOR PREVENTING NOCTURNAL ENURESIS

[76] Inventor: Myrna Hrubetz, 219 Locust North, Prescott, Wis. 54021

[21] Appl. No.: 325,456

[22] Filed: Mar. 17, 1989

[51] Int. Cl.$^5$ .............................................. A61F 5/48
[52] U.S. Cl. ...................................... 128/885; 128/79; 604/349
[58] Field of Search ............... 128/883, 885, 886, 157, 128/79, 87 A, 842, 844, 917, 918; 604/346, 347, 349, 353

[56] References Cited

U.S. PATENT DOCUMENTS

| | | | |
|---|---|---|---|
| 14,739 | 4/1856 | Sibley | 128/883 |
| 22,796 | 2/1859 | Gibbons | 128/883 |
| 36,314 | 8/1862 | Townsend | 128/883 |
| 87,932 | 3/1969 | Hoffman | 604/349 |
| 397,106 | 2/1889 | Bowen | 128/883 |
| 602,917 | 4/1898 | Scheinkman | 128/79 |
| 678,943 | 7/1901 | Davis | 128/883 |
| 714,850 | 12/1902 | Zimmerman | 128/885 |
| 765,261 | 7/1904 | Wise | 128/158 |
| 844,798 | 2/1907 | Hawley | 128/79 |
| 934,240 | 9/1909 | Tunnessen | 128/883 |
| 1,410,339 | 3/1922 | Martinka | 128/885 |
| 2,698,618 | 1/1955 | Evenstad | 128/138 |
| 3,612,047 | 10/1971 | Nesbit | 128/79 |
| 3,648,700 | 3/1972 | Warner | 128/79 X |
| 3,982,530 | 9/1976 | Storch | 126/79 |
| 4,429,689 | 2/1984 | Yanong | 128/79 |
| 4,475,910 | 10/1984 | Conway et al. | 604/352 |
| 4,675,012 | 6/1987 | Rooyakkers | 604/349 |
| 4,790,835 | 12/1988 | Elias | 604/349 |
| 4,795,450 | 1/1989 | Tovar et al. | 604/349 |

FOREIGN PATENT DOCUMENTS

| | | | |
|---|---|---|---|
| 7900374 | 7/1980 | Netherlands | 604/349 |
| 264690 | 1/1927 | United Kingdom | 604/349 |
| 2142243 | 1/1985 | United Kingdom | 604/349 |

Primary Examiner—Robert A. Hafer
Assistant Examiner—Kevin G. Rooney
Attorney, Agent, or Firm—Kinney & Lange

[57] ABSTRACT

A training device directed to helping prevent nocturnal enuresis in males. The device inlcudes a pair of elongated members for positioning along opposite sides of a penis. The elongated members are hinged together at one end allowing the elongated members to be folded toward one another around the opposite sides of the penis. An inelastic belt attached to one of the elongated members at a point between opposite ends of the belt can be wrapped around the members and the penis to press the members against the penis and thereby help avoid accidental dislodgement of the device. The elongated members have a semicircular cross section across the direction of elongation, the semicircular faces being oriented toward one another when the elongated members are folded parallel to one another. The inward orientation of the semicircular faces allows the device to be fitted relatively comfortably and aids in preventing dislodgement of the device. Upon enlargement of the penis the wearer is wakened by increased pressure applied substantially evenly all around the penis.

1 Claim, 1 Drawing Sheet

DEVICE FOR PREVENTING NOCTURNAL ENURESIS

TECHNICAL FIELD

The invention relates to a device for helping prevent nocturnal enuresis by males.

BACKGROUND OF THE INVENTION

It has been long known in the art that a penis enlarges and hardens prior to urination. This is true whether urination is voluntary or involuntary (enuresis). A number of devices have been proposed which use of this physical characteristic to prevent nocturnal enuresis.

Prior art devices are primarily directed to use of the pressure generated in the penis prior to urination to force a closing of the urethra preventing enuresis. For example, U.S. Pat. No. 1,410,339 issued Mar. 21, 1922 to Martinka taught fitting of an elastic band around the penis as a loop. A inwardly oriented portion of the loop was positioned beneath the urethra to be drawn into the urethra by any expansion or hardening of the penis, thus closing the urethra to urine flow.

U.S. Pat. No. 678,943 issued July 23, 1901 to Davis taught a "Compress" providing a ring positioned by semicircular saddles on a penis. The lower portion of the ring provided an inwardly disposed wedge to be brought against the urethra and pinch the urethra closed.

U.S. Pat. No. 714,850 issued Dec. 2, 1902 to Zimmermann provided rubber tubes held against the top and bottom of a penis by a spring apparatus. The tubes pinched the penis to prevent urination and upon enlargement of the penis disturbed the sleeping patient.

A common problem of the prior art devices is the use of pressure, usually applied to the urethra, to prevent urination. Application of pressure to the penis across a narrow focus can result in impeding the circulation of blood in the penis and application of unnecessary pain. While pain can provide a sure tool to waking the patient, and pinching the urethra a relatively sure method for preventing any occasion of enuresis, the absolute prevention of any occurrence of enuresis is not essential to treatment of a habit of nocturnal enuresis. It is sufficient in most cases to disturb the patient upon near occasion of enuresis. The focus of treatment is then directed to training the patient to break the tendency toward bed wetting, rather than the absolute prevention of any occasion of bed wetting. This purpose can be served by disturbing the patient's sleep frequently enough to prevent a substantial proportion of the occasions for bed wetting.

SUMMARY OF THE INVENTION

The present invention is directed to helping prevent nocturnal enuresis in males. The invention includes a pair of elongated members for positioning along opposite sides of a penis. The elongated members are hinged together at one end allowing the elongated members to be folded toward one another around the opposite sides of the penis. An inelastic belt attached to one of the elongated members at a point between opposite ends of the belt can be wrapped around the members and the penis to press the members against the penis and helping avoid accidental dislodgement of the device.

The opposite faces of the belt have fastening tape means disposed at opposite ends of the belt for cooperating to provide closure of the belt. The hinge between the members includes extensions for providing a position of the elongated members spaced from and parallel with respect to one another when folded on the hinge. The elongated members have a semicircular cross section across the direction of elongation, the indented semicircular faces being oriented toward one another when the elongated members are folded parallel to one another. The inward orientation of the semicircular faces allows the device to be fitted relatively comfortably to a penis and aids in preventing dislodgement of the device. Upon enlargement of the penis, the belt resists spreading of the members and increased pressure is applied substantially evenly around the penis. The sensation of pressure wakes the patient, who can then get up from bed, remove the device and use the toilet.

DETAILED DESCRIPTION OF THE PREFERRED EMBODIMENT

Figure 1:
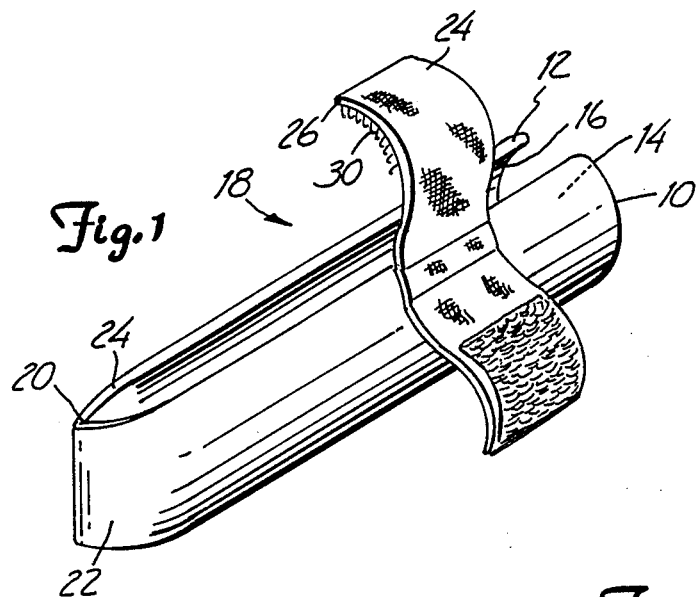
FIG. 1 is a perspective view of a device for preventing male nocturnal enuresis.
Figure 2:
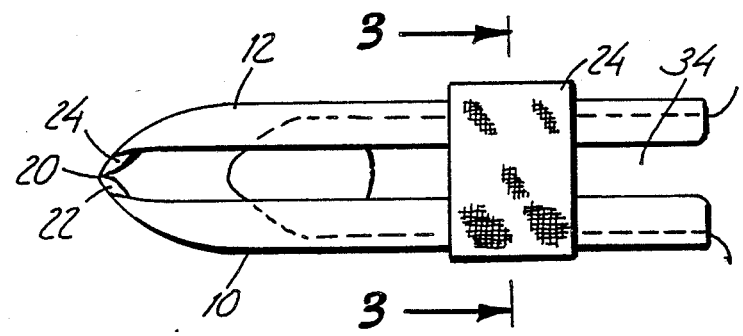
FIG. 2 is a side elevation view of a device.
Figure 3:
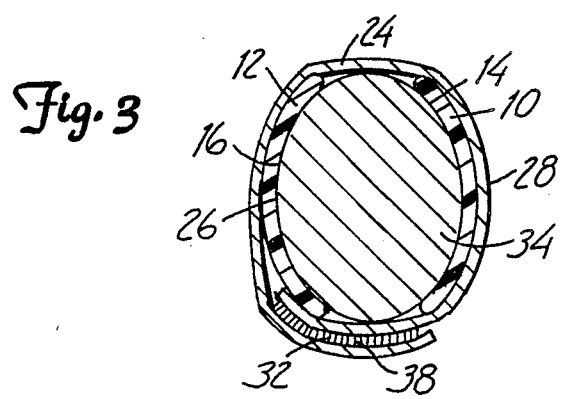
FIG. 3 is a cross sectional view taken along line 3—3 of FIG. 2.
Figure 4:
FIG. 4 is an enlarged view of a hinge portion of the device.

FIGS. 1–4 illustrate the device, which comprises two elongated members 10 and 12. Elongated members 10 and 12 are illustrated positioned substantially parallel to one another but can be opened outwardly on hinge 20. Members 10 and 12 are arcuate sections along a substantial portion of the lengths of the members. Thus, a substantial length of inner faces 14 and 16 of members 10 and 12 are concave in planes perpendicular to the direction of elongation of the members. Closure of members 10 and 12 to a position where indented inner faces 14 and 16 face one another forms a slitted tube like structure 18, which can be positioned comfortably on a penis.

Elongated members 10 and 12 are attached at one end of each member, respectively, by a hinge 20. Hinge 20 includes extension members 22 and 24, which are portions of elongated members 10 and 12 near the ends of the elongated members. Extension members 22 and 24 are bent inwardly with respect to inner faces 14 and 16 of the elongated members to space the elongated members when folded on hinge 20 to positions parallel to one another.

Elongated members 10 and 12 with extension members 14 and 16 can be formed from a single semicircular piece of molded or extruded resilient plastic. Formation of a crease line at the midpoint of the plastic piece provides hinge 20. Appropriate trimming of the piece avoids sharp or jagged edges which could cause discomfort to a wearer. Use of a plastic type material permits easy cleaning of the device.

Retention of elongated members 10 and 12 on a penis is provided by a closure strap 24 which is shown attached to elongated member 10. Closure strap 24 is a relatively inelastic belt which wraps latitudinally around folded elongated members 10 and 12. Inner face 26 of closure strap 24 has an area 30 of closure tape (such as Velcro( TM )) applied to one end thereof. Outer face 28 of closure strap 24 has an area 32 of closure tape applied to the opposite end of the strap relative to area 30. Thus, when strap 24 is wrapped around a penis 34 and elongated members 10 and 12, areas 28 and 32 are brought adjacent one another (FIG. 3) and cooperate for maintaining a snug fit of the device on a flaccid penis.

The device is fitted to a penis by positioning folding elongated members 10 and 12, inner faces 14 and 16 first, onto opposite sided of the penis. The bottom of the penis is open to a gap between elongated members 10 and 12 and thus the urethra and various blood vessels are not pinched. The head of a penis 34 is spaced from hinge 20 and the ends of elongated members 10 and 12 to avoid excessive pinching as well. Closure strap 24 may be closed at a point snug but not excessively tight around the penis. Upon an increase of pressure or enlargement of the penis the fit of the device will become noticeably tighter to the wearer. The sensation of increasing pressure wakes the wearer and alerts him to get up to use a toilet. The device can be easily removed by the wearer, and repositioned after removal to permit use of the toilet.

Although the present invention has been described with reference to preferred embodiments, workers skilled in the art will recognize that changes may be made in form and detail without departing from the spirit and scope of the invention.

What is claimed is:

1. A device for training men and boys in breaking a habit of nocturnal enuresis comprising:
   a pair of elongated, resilient members;
   the elongated members being hinged together at one end thereby allowing the elongated members to be folded to positions opposite one another on opposite sides of a penis;
   the members including extensions leading to the hinge for providing a position of the elongated members spaced from and parallel with respect to one another when folded;
   the elongated members having a semicircular cross section across the direction of elongation with indented semicircular faces being oriented toward one another when the elongated members are folded;
   an inelastic belt attached to one of the elongated members at a point between opposite ends of the belt, the belt being wrapable around the members to hold the members gently against the penis when it is in a flaccid state;
   the inelastic belt resisting unfolding of the members and applying increased pressure substantially evenly to the penis upon enlargement of the penis prior to urination; and
   fastening tape applied to cooperating ends of the inelastic belt providing a belt which can be repeatedly opened and closed.

* * * * *